United States Patent [19]
Phlipot et al.

[11] Patent Number: 5,728,145
[45] Date of Patent: Mar. 17, 1998

[54] THERMAL BLANKET WITH CENTRAL AIR INLET

[75] Inventors: Thomas H. Phlipot, Jackson; Raymond G. Ragan, Marshall, both of Mich.; Joseph A. Namenye, Elkhart, Ind.; James G. Stephenson, Marshall, Mich.

[73] Assignee: Progressive Dynamics, Inc., Marshall, Mich.

[21] Appl. No.: 686,603

[22] Filed: Jul. 22, 1996

[51] Int. Cl.[6] .................................................. A61F 7/00
[52] U.S. Cl. ............................................................ 607/104
[58] Field of Search ............................ 607/96, 104, 107, 607/108, 114; 165/46; 5/284, 423

[56] References Cited

U.S. PATENT DOCUMENTS

| | | |
|---|---|---|
| D. 359,810 | 6/1995 | Namenye. |
| D. 362,507 | 9/1995 | Zuck et al.. |
| 4,572,188 | 2/1986 | Augustine et al.. |
| 5,106,373 | 4/1992 | Augustine et al.. |
| 5,125,238 | 6/1992 | Ragan et al.. |
| 5,184,612 | 2/1993 | Augustine. |
| 5,265,599 | 11/1993 | Stephenson et al.. |
| 5,300,102 | 4/1994 | Augustine et al.. |
| 5,324,320 | 6/1994 | Augustine et al.. |
| 5,350,417 | 9/1994 | Augustine. |
| 5,360,439 | 11/1994 | Dickerhoff et al. .................. 607/96 X |
| 5,392,847 | 2/1995 | Stephenson. |
| 5,405,371 | 4/1995 | Augustine et al.. |
| 5,443,488 | 8/1995 | Namenye et al.. |
| 5,545,194 | 8/1996 | Augustine .......................... 607/108 X |

*Primary Examiner*—Jennifer Bahr
*Assistant Examiner*—Samuel Gilbert
*Attorney, Agent, or Firm*—Young & Basile, P.C.

[57] ABSTRACT

A thermal blanket for flowing temperature controlled air upon a patient wherein the blanket is inflated with air and orifices within the blanket permit the air to flow upon the patient. The improvement includes the locating of the air inlet at a central blanket location in the patient's chest region to permit the highest air temperature to be available over the chest region, and the air flow direction produces optimum distribution. The locating of the air hose upon the blanket upper side permits the inflated blanket to insulate the hose from the patient, the portion of the blanket placed over the patient's head is perforated to facilitate forming a head receiving opening, and a transparent barrier may be affixed to the blanket upper side to cover the patient's face during respiration.

12 Claims, 1 Drawing Sheet

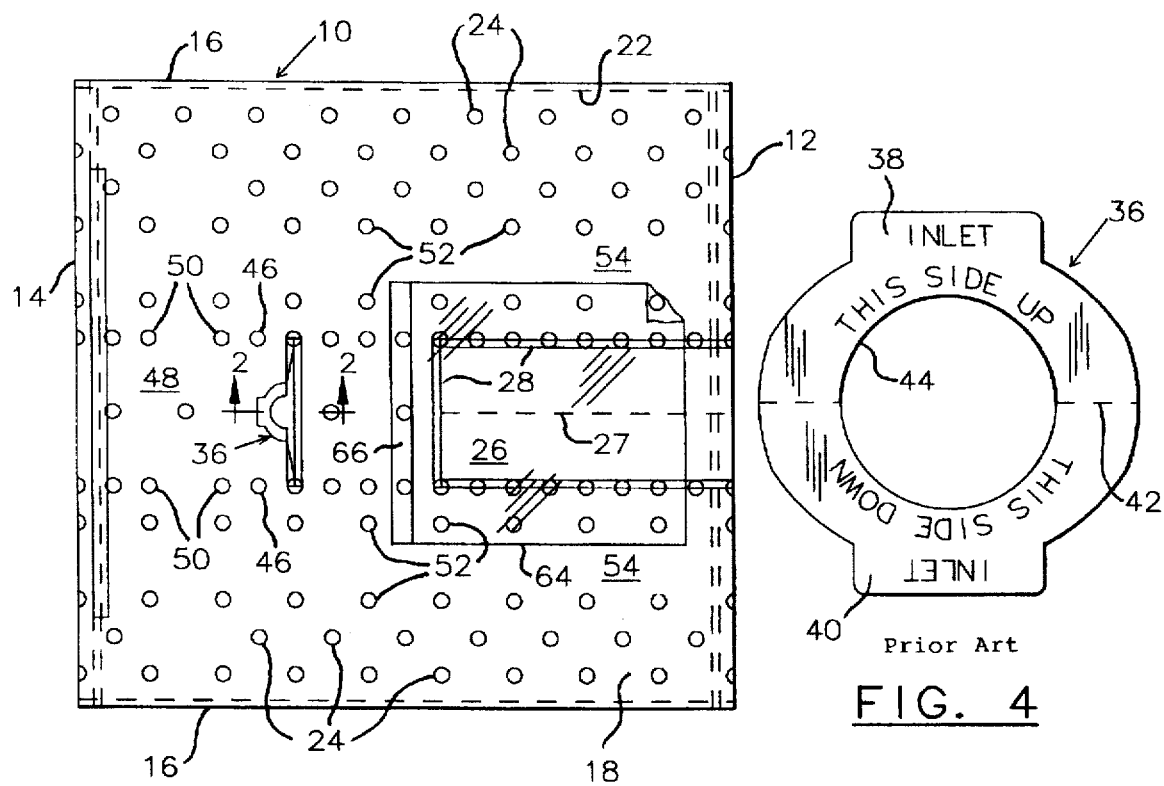
FIG. 1
FIG. 4 Prior Art
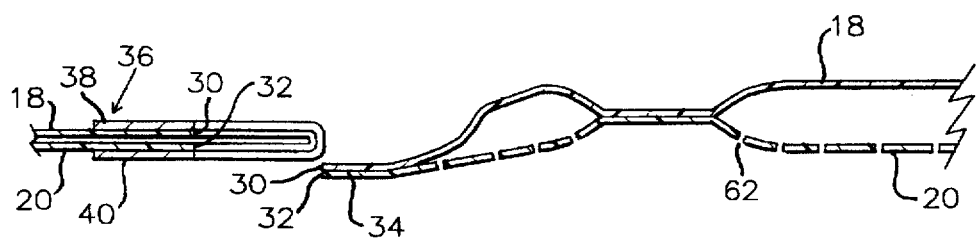
FIG. 2
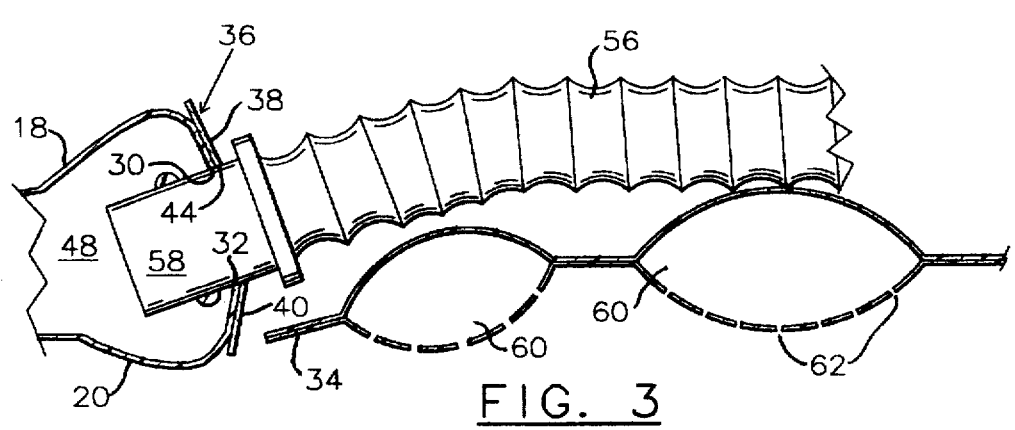
FIG. 3

5,728,145

THERMAL BLANKET WITH CENTRAL AIR INLET

BACKGROUND OF THE INVENTION

1. Field of the Invention

The invention pertains to thermal blankets used for medical purposes to control the body temperature of post-surgery patients and the like wherein a controlled temperature air flows from the blanket upon the patient.

2. Description of the Related Art

Thermal blankets are employed to control the body temperature of patients before, during and after surgery, wherein a warmed air, or a cooled air, inflates a blanket placed over the patient and orifices located in the bottom surface of the blanket direct air within the blanket upon the patient. Blankets of this type may be made at low cost as to be disposable, and typical samples of this type of blanket are shown in the assignee's U.S. Pat. Nos. 5,125,238; 5,265,599; 5,392,847; 5,443,488; Des. 359,810 and Des. 362,507.

In the aforementioned patents, the port communicating with the blanket receiving the air supply is located within the lower peripheral edge of the blanket remote from the patient's head. This port is of a foldable nature permitting the blanket to be flatly folded for shipping purposes. Inflation of the blanket is controlled by a plurality of tacks or heat seals between the upper and lower blanket sheets wherein the blanket inflates in a "quilted" manner, and the air flow throughout the blanket from the port can be controlled by employing a pre-determined spacing between the tacks or heat seals as shown in U.S. Pat. No. 5,265,599.

Prior art thermal blankets of this type use heated air which is introduced at the lower or foot end of the blanket, and this construction permits the air to cool before it reaches the patient's upper torso portions. Also, locating the heated air port at the foot end of the blanket limits the location of the hot air blower.

OBJECTS OF THE INVENTION

It is an object of the invention to provide a thermal blanket using temperature controlled air which is capable of impinging concentrated air flow upon the chest region of a patient with ease of access and improved efficiency.

Another object of the invention is to provide a thermal blanket inflated by pressurized air wherein the pressurized air is introduced into the blanket at a location central with respect to the blanket periphery using an inlet which is easy to manufacture.

An additional object of the invention is to provide a thermal blanket inflated with a temperature controlled air wherein the air is introduced into the blanket intermediate the blanket periphery and the air supply hose is insulated from the patient by the inflated blanket.

A further object of the invention is to provide improvements in head, neck and face coverings wherein seal surfaces and insulating material is efficiently incorporated in the overall blanket assembly, and the blanket provides options with respect to the nature of the patient's head access and head covering.

SUMMARY OF THE INVENTION

The thermal blanket of the invention may be of a smaller dimension than a "full" body blanket, and may be used to specifically control the temperature of the patient's chest region. The blanket includes upper and lower thermoplastic sheets heat sealed together at their periphery, and a plurality of spaced tacks heat seal the upper and lower sheets together at pre-determined locations to control the extent of blanket inflation. A plurality of orifices in the lower sheet permit the temperature regulated air within the inflated blanket to impinge upon the patient for body temperature control purposes.

In the instant invention, the port in which the air supply hose is inserted is located at a central region with respect to the blanket periphery. Preferably, a foldable port of the type shown in U.S. Pat. No. 5,125,238 is employed which may be economically produced and folds flat with the blanket for concise storage dimensions. The blanket is slit within its central region to provide an attachment portion for the port, and the inventive concepts do not detract from the concise flat foldable characteristics of the disposable temperature control blanket of the invention. The instant invention augments the use of the centrally located port by providing a new type of access central to the blanket.

The ability of the blanket to impinge a higher temperature of air upon the patient in the chest region, in addition to centrally locating the air supply port, is due to the spacing of the heat seal tacks adjacent the port so as to laterally disperse the incoming air into lateral passages defined in the blanket having reduced air flow characteristics as those blanket portions immediately adjacent the lateral edges. Such spacing of the tacks permits a rapid flow of air through the blanket to those blanket portions most desirable with respect to the distribution of air with little temperature loss.

As the air supply hose inserted into the centrally located port will lie upon the inflated blanket, access to the patient's lower regions is improved as compared with blankets having lower air supply hoses, and although the air supply hose may pass over the patient's chest region, localized overheating due to exposure to the hose is prevented as the inflated blanket is located between the patient's body and the air hose, and the inflated blanket functions as a thermal barrier to protect the patient from the hose. The central hose location also allows a more varied location for the blower unit providing pressurized air to the blanket.

BRIEF DESCRIPTION OF THE DRAWINGS

The aforementioned objects and advantages of the invention will be appreciated from the following description and accompanying drawings wherein:

FIG. 1 is a plan view of a thermal blanket constructed in accord with the invention, FIG. 2 is an enlarged elevational sectional detail view as taken along Section 2—2 of FIG. 1, FIG. 3 is an enlarged elevational sectional detail view as taken along Section 2—2 of FIG. 1 illustrating the relationship of the air supply hose to the blanket fitting during inflation, and FIG. 4 is an elevational detail view of the blanket port when unfolded.

DESCRIPTION OF THE PREFERRED EMBODIMENT

In FIG. 1, the general rectangular configuration of a thermal blanket 10 utilizing the concepts of the invention is illustrated wherein the size of the blanket is such as to cover the patient's chest region. The periphery of the blanket includes an upper edge 12, a lower edge 14, and lateral edges 16. The specific construction of the blanket is best appreciated from the disclosure of U.S. Pat. No. 5,125,238, the composition of the blanket 10 being identical to the blanket illustrated in such patent. The blanket 10 includes a top sheet 18 of a thermoplastic material and a lower sheet 20, likewise of a thermoplastic material having a high friction material or layer exteriorly bonded thereto. The periphery of the blanket 10 is heat sealed at 22.

Intermediate the periphery edges of the blanket, heat seal tacks 24 bonding the sheets 18 and 20 together control the extent of blanket inflation, and as will be appreciated from FIG. 1, the tacks 24 are offset with respect to adjacent rows as to permit air flow within the blanket between the tacks.

The blanket neck region 26 is defined by tacks and is heat sealed at 28 wherein the neck region 26 will not be inflated during use, as later described. The neck region 26 is provided with a line of perforations 27 parallel to the lateral edges 16, as will be appreciated in FIG. 1. The use of the perforations 27 is described later.

The blanket 10 is centrally slit between the lateral edges 16, and the innermost edge of the neck region 26 and the lower edge 14. This slit produces an upper sheet slit edge 30 and a lower sheet slit edge 32, FIGS. 2 and 3, and the regions of the sheets 18 and 20 adjacent the slit and toward the neck region 26 are heat sealed together in an airtight manner as shown at 34 in FIGS. 2 and 3.

A foldable port 36 is mounted upon the portion of the slit edges 30 and 32 disposed toward the blanket lower edge 14. The port 36 includes an upper flap 38 which is bonded to the top sheet 18, and the port lower flap 40 is bonded to the lower sheet 20. The port 36 is formed of a stiff paper or similar material and includes a fold line 42, FIG. 4, and a circular opening 44. The port 36 is identical to the folding port shown in U.S. Pat. No. 5,125,238 and operates in an identical manner.

The blanket 10 includes a plurality of central tacks 46 spaced in the manner as will be apparent from FIG. 1. The central tacks 46 are closer together than the tacks 24 and define a relatively open passage or chamber 48 immediately to the left of the port 36 as shown in FIGS. 1–3. Tacks 50 adjacent the passage 48 are spaced apart a greater distance than the tacks 46 and define lateral openings in the passage 48 wherein airflow within passage 48 will easily flow laterally, and lateral passage tacks 52 define lateral passages 54 into which air flowing from the passage 48 will readily flow. As will be appreciated from FIG. 1, the spacing between the passage tacks 52 on opposite sides of a common passage 4 is greater than the spacing between tacks 24 producing an enlarged passage 54 which facilitates air flow from the passage 48 into the lateral regions of the blanket between the upper edge 12 and the lower edge 14. From the passages 54, the air will flow toward the lateral edges 16 intermediate the tacks 24.

With reference to FIG. 3, an air supply hose 56 is illustrated having a tubular conical nose 58. The hose 56 is supplied with pressurized air from a heated air supply, not shown, such as may be supplied from apparatus shown in U.S. Pat. No. 5,300,098.

Upon unfolding or opening the port flaps 38 and 40, as shown in FIG. 3, the port opening 44 will be of a circular configuration as to closely receive the conical hose nose 58 as shown in FIG. 3 whereby heated air will be introduced into the blanket passage 48 and flow laterally into the passages 54 as described above.

As the hose 54 will lie upon the chest of the patient, the blanket chambers 60 directly located below the hose 56 will support the hose and act as thermal insulation between the hose and the patient's body preventing a localized overheating of the patient's body directly below the hose.

The blanket 10, because it is not normally utilized over the entire body of the patient, and because the port 36 is located at the central region of the blanket and lateral airflow into the passages 54 readily occurs, the temperature of the blanket 10 can remain relatively high with little heat loss therethrough so that the heated air within the blanket 10 when inflated may flow through the orifices 62 in the lower sheet 20 as described in U.S. Pat. No. 5,125,238. Because the blanket 10 is normally utilized at the upper torso of the patient, the neck and head region 26 may be located over the patient's head. In such instance, the uninflated neck and head portion 26 can be opened by separating the portion 26 along the perforations 27. Such action will produce flaps at the region 26 permitting the patient's face and head to extend therethrough. Also, in instances where the patient is using a respirator, and a high body temperature is desired, a clear plastic flap or sheet 64 may be taped to the upper surface of the blanket at 66 wherein upon the patient's head protruding through the region 26, the flap 64 may be positioned over the patient's face and yet the transparent nature of the flap permits the patient's face and eyes to be observed.

It is appreciated that various modifications to the inventive concepts may be apparent to those skilled in the art without departing from the spirit and scope of the invention.

We claim:

1. A thermal blanket having a periphery formed by upper and lower superimposed flexible sheets sealed together at the periphery defining an envelope and sealed together by a plurality of spaced tacks intermediate the blanket periphery to control expansion during inflation, a plurality of air flow exit orifices defined in the lower sheet and an inlet affixed to said sheets for receiving an air supply fitting for inflating the blanket, the improvement comprising the upper and lower sheets being slit at a location within the blanket periphery defining first and second upper and lower sheet regions adjacent said slit, the upper and lower sheets of said first sheet region being sealed together, the inlet comprising a foldable inlet port having an air supply fitting receiving opening defined therein having a first fold portion and a second fold portion, said fold portions being hinged together along a hinge line, said port being attached to the envelope at said second sheet region by said fold portions, said first fold portion being sealed to the envelope upper sheet and said second fold portion being sealed to the envelope lower sheet whereby said port seals said second sheet region.

2. The thermal blanket as in claim 1 further comprising, said foldable port being formed of a stiff sheet material.

3. The thermal blanket as in claim 2 further comprising, said foldable port being formed of a paper material.

4. The thermal blanket as in claim 2 further comprising, said foldable port being formed of a synthetic plastic material.

5. The thermal blanket as in claim 1 further comprising wherein the blanket includes an upper edge and a lower edge, said inlet port being located between said upper and lower edges and said inlet port opening extending toward said upper edge wherein an air supply conduit having an air supply fitting received within said port opening will extend toward said upper edge during blanket inflation.

6. The thermal blanket as in claim 5 further comprising, the air flowing from the conduit fitting during blanket inflation being directed toward said blanket lower edge and a manifold region defined by the blanket upper and lower sheets intermediate said slit and said lower edge, low air flow resistant passages defined between the blanket upper and lower sheets by the tacks extending between said blanket upper and lower edges on opposite sides of the inlet port, said manifold region communicating with said passages.

7. The thermal blanket as in claim 1 further comprising, the thermal blanket periphery including upper, lower and lateral edges, the upper and lower sheets being slit intermediate said upper and lower edges and said lateral edges.

8. The thermal blanket as in claim 7 further comprising, said slit having a length substantially parallel to said upper and lower blanket edges.

9. The thermal blanket as in claim 7 further comprising, a non-inflatable neck and head region defined in said blanket intersecting said blanket upper edge, said neck region including an inner edge located intermediate said blanket upper and lower edges, said slit being defined in said blanket intermediate said neck region inner edge and said blanket lower edge.

10. The thermal blanket as in claim 9 further comprising, perforations defined in said non-inflatable neck and head region intersecting said blanket upper edge, said perforations permitting said neck and head region to be opened to provide access for the patient's head and neck.

11. The thermal blanket as in claim 9 further comprising, a flexible head drape formed of a transparent material having an edge affixed to the upper sheet wherein said head drape may be positioned over a patient's face extending through the blanket head and neck region.

12. The thermal blanket as in claim 11 further comprising, said head drape being affixed to the blanket upper sheet at a location intermediate said neck region inner edge and said slit.

* * * * *